United States Patent
Ji et al.

(10) Patent No.: US 10,314,937 B2
(45) Date of Patent: Jun. 11, 2019

(54) BIOCOMPATIBLE HEMOSTATIC PRODUCT AND PREPARATION METHOD THEREOF

(71) Applicant: EndoClot Plus Co., Ltd., Suzhou, Jiangsu (CN)

(72) Inventors: Xin Ji, Suzhou (CN); Cheng Xing, Suzhou (CN); Heng Zhang, Suzhou (CN)

(73) Assignee: Endoclot Plus Co., Ltd., Jiangsu (CN)

( * ) Notice: Subject to any disclaimer, the term of this patent is extended or adjusted under 35 U.S.C. 154(b) by 0 days.

(21) Appl. No.: 15/511,300

(22) PCT Filed: Sep. 2, 2015

(86) PCT No.: PCT/CN2015/088844
§ 371 (c)(1),
(2) Date: Mar. 15, 2017

(87) PCT Pub. No.: WO2016/041443
PCT Pub. Date: Mar. 24, 2016

(65) Prior Publication Data
US 2017/0252479 A1    Sep. 7, 2017

(30) Foreign Application Priority Data

Sep. 18, 2014 (CN) .......................... 2014 1 0478818

(51) Int. Cl.
| | | |
|---|---|---|
| *A61K 9/14* | (2006.01) | |
| *A61P 17/02* | (2006.01) | |
| *A61L 15/26* | (2006.01) | |
| *A61L 15/44* | (2006.01) | |
| *A61L 15/46* | (2006.01) | |
| *A61L 24/00* | (2006.01) | |
| *A61L 24/04* | (2006.01) | |
| *A61L 26/00* | (2006.01) | |
| *C08L 71/02* | (2006.01) | |

(52) U.S. Cl.
CPC ............ *A61L 26/0019* (2013.01); *A61K 9/14* (2013.01); *A61L 15/26* (2013.01); *A61L 15/44* (2013.01); *A61L 15/46* (2013.01); *A61L 24/0015* (2013.01); *A61L 24/0026* (2013.01); *A61L 24/043* (2013.01); *A61L 24/046* (2013.01); *A61L 26/0052* (2013.01); *A61L 26/0061* (2013.01); *A61L 26/0066* (2013.01); *A61L 26/0076* (2013.01); *A61P 17/02* (2018.01); *A61L 2300/418* (2013.01); *A61L 2300/60* (2013.01); *A61L 2400/04* (2013.01)

(58) Field of Classification Search
CPC ........ C08L 71/02; A61L 15/26; A61L 24/046; A61L 26/0019; A61L 15/44; A61L 15/46; A61L 2300/418; A61L 2300/60; A61L 2400/04; A61L 24/0015; A61L 24/0026; A61L 24/043; A61L 26/0052; A61L 26/0061; A61L 26/0066; A61L 26/0076
See application file for complete search history.

(56) References Cited

U.S. PATENT DOCUMENTS

| | | |
|---|---|---|
| 471,865 A | 3/1892 | Howard |
| 576,437 A | 2/1897 | Elliott |
| 881,238 A | 3/1908 | Hasbrouck |
| 1,685,280 A | 9/1928 | Findley |
| 1,732,566 A | 10/1929 | McKendrick |
| 1,934,793 A | 11/1933 | Crain |
| 2,122,234 A | 6/1938 | McAuliffe |
| 2,151,418 A | 3/1939 | Brown |
| 2,185,927 A | 1/1940 | Shelanski |
| 2,570,774 A | 10/1951 | Davis |
| 3,419,006 A | 12/1968 | King |
| 4,184,258 A | 1/1980 | Barrington |
| 4,616,644 A | 10/1986 | Saferstein |
| 5,273,531 A | 12/1993 | Knoepfler |
| 5,312,331 A | 5/1994 | Knoepfler |
| 5,445,612 A | 8/1995 | Terakura |
| 5,599,297 A | 2/1997 | Chin |
| 5,800,381 A | 9/1998 | Ognier |
| 5,874,500 A | 2/1999 | Rhee |

(Continued)

FOREIGN PATENT DOCUMENTS

| | | |
|---|---|---|
| CN | 86103931 A | 12/1986 |
| CN | 101091803 A | 12/2007 |

(Continued)

OTHER PUBLICATIONS

International Search Report for PCT/CN2015/088844, dated Dec. 8, 2015.

(Continued)

*Primary Examiner* — Mark V Stevens
(74) *Attorney, Agent, or Firm* — Novel IP

(57) ABSTRACT

Provided herein are a biocompatible hemostatic product and a tissue sealant, including polyethylene oxide particles with a viscosity-average molecular weight ranging from 100,000 to 7,000,000 Daltons, a particle size ranging from 0.5 µm to 2000 µm and a water absorbency capacity ranging from 1 to 500 times of its own weight. Also provided herein is a method for preparing biocompatible hemostatic product and tissue sealant and the use of the biocompatible hemostatic product and tissue sealant in hemostasis, preventing adhesion, avoiding infection, promoting tissue healing, and sealing wound of tissues and organs either on animal's body surface, or inside body's cavity.

24 Claims, 5 Drawing Sheets

(56) References Cited

U.S. PATENT DOCUMENTS

| | | | |
|---|---|---|---|
| 5,951,531 A | 9/1999 | Ferdman | |
| 6,312,725 B1 | 11/2001 | Wallace | |
| 6,610,005 B1 | 8/2003 | Tao | |
| 7,427,607 B2 | 9/2008 | Suzuki | |
| 7,547,292 B2 | 6/2009 | Sheldrake | |
| 8,575,132 B2 | 11/2013 | Ji | |
| 8,721,582 B2 | 5/2014 | Ji | |
| 8,827,980 B2 | 9/2014 | Ji | |
| 9,629,966 B2 | 4/2017 | Ji | |
| 2003/0181917 A1 | 9/2003 | Gertner | |
| 2004/0096507 A1* | 5/2004 | Kwang | A61K 9/0014 424/486 |
| 2008/0021374 A1 | 1/2008 | Kawata | |
| 2008/0214989 A1 | 9/2008 | Kawata | |
| 2009/0062233 A1 | 3/2009 | Ji | |
| 2010/0035886 A1* | 2/2010 | Cincotta | A61K 9/0019 514/250 |
| 2011/0066132 A1 | 3/2011 | Ji | |
| 2011/0178495 A1* | 7/2011 | Ji | A61M 13/00 604/500 |
| 2013/0046278 A1 | 2/2013 | Ji | |
| 2013/0108671 A1 | 5/2013 | McCoy | |
| 2013/0123213 A1 | 5/2013 | Ji | |
| 2013/0131621 A1 | 5/2013 | Van Holten | |
| 2013/0255538 A1 | 10/2013 | Lu | |
| 2014/0207097 A1 | 7/2014 | Ji | |

FOREIGN PATENT DOCUMENTS

| | | | |
|---|---|---|---|
| CN | 101121041 A | 2/2008 | |
| CN | 101455857 A | 6/2009 | |
| CN | 101485897 A | 7/2009 | |
| CN | 101497670 A | 8/2009 | |
| CN | 101785873 A | 7/2010 | |
| CN | 102019028 B | 4/2011 | |
| CN | 105412975 A | 3/2016 | |
| EP | 0206697 A2 | 12/1986 | |
| EP | 1523994 A1 | 4/2005 | |
| EP | 3228331 A | 10/2017 | |
| EP | 3228331 A1 | 10/2017 | |
| JP | 2017527416 A | 9/2017 | |
| KR | 2617792 A2 * | 7/2013 | A61K 9/7007 |
| KR | 20140100245 A | 8/2014 | |
| KR | 20170060054 A | 5/2017 | |
| WO | 2016041443 A1 | 3/2016 | |

OTHER PUBLICATIONS

Natour et al., "Assessment of the effect on blood loss and transfusion requirements when adding a polyethylene glycol sealant to the anastomotic closure of aortic procedures: a case-control analysis of 102 patients undergoing Bentall procedures" J Cardiothorac Surg. 2012; 7: 105. Published online Oct. 8, 2012. doi: 10.1186/1749-8090-7-105.

Database WPI Week 201068 Thomson Scientific, London, GB; AN 2010-K65387 XP002784440, & CN101785873A (JI X) Jul. 28, 2010.

N. N. : "Polyox TM WSR 301 Amerchol", The DOW Chemical Company Sales Specification, 2012, XP002784406.

N. N. : "Polyox TM Water Soluble Resins", DOW, Oct. 2013, XP002784441.

Supplementary European Search Report for EP15841194, completed on Sep. 5, 2018.

Office Action dated Mar. 1, 2019 for Chinese Patent Application No. 201410478818.4.

* cited by examiner

BIOCOMPATIBLE HEMOSTATIC PRODUCT AND PREPARATION METHOD THEREOF

CROSS REFERENCE TO RELATED APPLICATIONS

The present application is a National Stage application of PCT Application No. PCT/CN2015/088844 under 35 U.S.C. 371, which, in turn, claims priority from Chinese Patent Application Serial No. 201410478818.4, filed on Sep. 18, 2014, entitled "A Biocompatible Hemostatic Product and A Method for Preparing the Same", the entire disclosures of which are herein incorporated by reference.

FIELD

Described herein are a biocompatible hemostatic product and tissue sealant as well as a method for preparing the same. In particular, the present disclosure relates to a biocompatible hemostatic product and tissue sealant with high water absorbency capacity, which can be topically applied onto the wound of human and other mammal's tissues and organs, caused by surgeries (including minimally invasive surgeries) and trauma, for hemostasis, sealing wound, reducing exudation, promoting tissue healing, protecting wound surface and avoiding infection. Moreover, the present disclosure also relates to a method for preparing said biocompatible hemostatic product and tissue sealant.

BACKGROUND

Generally, surgeries and trauma cause wound bleeding resulting in blood loss, and thus hemostasis is needed immediately. Surgeons also need to seal the wounds caused by surgical procedures, so as to prevent the wounds from re-bleeding and infection.

Hemostatic products commonly used for treating wounds can be classified in the following categories:
 1. Hemostatic dressing including bandages, hemostatic sponges and gauzes and the like;
 2. Hemostatic film or hemostatic glue;
 3. Hemostatic powder.

Hemostatic products (e.g., the hemostatic materials used during surgical procedure) applied to the inside of tissues and organs of body are normally those materials that can be degraded by enzymes or engulfed by phagocytes in the human body. Therefore, the hemostatic products can be degraded or metabolized after applying hemostatic products for a certain time period.

Hemostatic products applied onto the body surface or surfaces of a body cavity (orifice) (e.g., upper respiratory tract, digestive tract, genital tract etc.) are normally those materials that are not necessarily required to be degraded by enzymes or engulfed by phagocytes in human body. These hemostatic products can be removed or peeled off with the scar after applying for a certain time period, and then discharged out of the body.

Polyoxyethylene (PEO) is also known as polyethylene oxide. It is a commonly used medical polymer and often used as an excipient or a plasticizer suitable for the medicaments in manufacturing medical binders or tablets. The structural unit of PEO is —[$CH_2CH_2O$]—, and the molecular weight of PEO varies in a wide range. PEO with a relative molecular weight ranging from 200 to 20,000 Daltons is a viscous liquid or waxy solid. PEO with a relative molecular weight ranging from $1\times10^5$ to $1\times10^6$ Daltons is a white, flowable powder.

The molecular weight of a synthetic polymer typically has polydispersity. In a general sense, the molecular weight of polymer refers to an average molecular weight. Depending on the methods for statistics of average molecular weight, the average molecular weight of polymer can be further defined as number-average molecular weight, weight-average molecular weight, Z-average molecular weight and viscosity-average molecular weight. Among them, the viscosity-average molecular weight refers to molar weight of polymer, which is measured using viscosity method. In various polymers, linear polymers have high solution viscosity and the viscosity value has a correlation with molecular weight, therefore, the molecular weight of linear polymers is typically measured using the viscosity method. Moreover, devices used in the viscosity method are simple, easy for operation, suitable for a wide range of molecular weights and can achieve high accuracy. Measuring viscosity-average molecular weight by using the viscosity method is a common experimental technology for one having ordinary skill in the polymer field (see, for example, LI Jinsong et al., "Measurement for Viscosity-average Molecular Weight of Polyethylene Oxide Wax", SHANDONG CHEMISTRY, Vol. 35, 2006; YUAN Jinying, et al., "Measurement for Viscosity-average Molecular Weight of Polyethylene Glycol", POLYMER MATERIALS AND ENGINEERING, Vol. 15, No. 4, 1999).

Hemostatic bandages and gauzes commonly used to stop bleeding, protect wounds, avoiding re-bleeding and infection are based on the principle of compression by bandaging. Recently, it has been reported that natural hemostatic polysaccharide (e.g., chitosan, cellulose and the like) and synthetic polymer materials are coated on the surface of a fabric dressing after being dissolved in liquid, so as to form hemostatic adhesive bandages for hemostasis. For example, Chinese patent application CN86103931 discloses an adhesive bandage, which consists of a backing coated with pressure-sensitive adhesive, an absorbent pad fixed on the backing, and a perforated plastic film wound release cover overlaid on the absorbent pad, wherein a coating comprising polyethylene oxide having a molecular weight of at least 600,000 Daltons is provided on the wound release cover. The bandage disclosed in this Chinese patent application comprises polyethylene oxide with a low molecular weight, and use of this hemostatic product in the form of bandage has some deficiencies, for example, such bandage cannot be used for a bleeding wound surface within body or body cavity orifice (e.g., interior surface of digestive tract).

Additionally, hemostatic glue (e.g., hydrogel and sealant glue) prepared with polysaccharide or synthetic polymer can be applied topically on the sutured skin wound or wound on the body surface caused by trauma for the purpose of protecting the wound, avoiding exudation of fluid and preventing infection. Such hemostatic glue is readily used for the wound on the body surface, but cannot be applied on the bleeding wound surface within the body cavity (e.g., interior surface of digestive tract).

So far, there has been no report about applying PEO powders topically on internal wounds for the purpose of hemostasis and wound sealing.

Therefore, there is a need for a hemostatic product which is convenient for use, has excellent efficacy on both hemostasis and wound sealing. It can be applied topically on a wound surface or a bleeding wound surface within the body cavity orifice via ancillary devices, such as specific delivery device for administration by virtues of endoscope, so as to achieve rapidly hemostasis, form polymer-blood glue matrix, seal the wound and avoid re-bleeding.

SUMMARY

In one aspect, provided herein is a biocompatible hemostatic product, comprising polyethylene oxide (PEO) particles, wherein polyethylene oxide has a viscosity-average molecular weight ranging from 100,000 to 7,000,000 Daltons, the polyethylene oxide particles have a particle size ranging from 0.5 µm to 2000 µm and a water absorbency capacity ranging from 1 to 500 times of its own weight; and wherein after absorbing water, the hemostatic product forms glue for sealing the bleeding wound surface.

In another aspect, provided herein is a biocompatible tissue sealant, comprising polyethylene oxide (PEO) particles, wherein, polyethylene oxide has a viscosity-average molecular weight ranging from 100,000 to 7,000,000 Daltons, the polyethylene oxide particles have a particle size ranging from 0.5 µm to 2000 µm and a water absorbency capacity ranging from 1 to 500 times of its own weight; and wherein after applying onto the wound surface from which exudate oozes, the tissue sealant forms a glue to seal the wound surface from which the exudate oozes.

The polyethylene oxide described herein has a viscosity-average molecular weight preferably ranging from 500,000 to 7,000,000 Daltons, more preferably from 600,000 to 4,000,000 Daltons, even more preferably from 800,000 to 4,000,000 Daltons.

The polyethylene oxide particles described herein have a particle size preferably ranging from 10 µm to 500 µm, more preferably from 10 µm to 300 µm, most preferably from 30 µm to 250 µm.

The polyethylene oxide particles described herein have a water absorbency capacity preferably ranging from 2 to 100 times of its own weight.

The polyethylene oxide particles described herein preferably have a viscosity of a 6.67% aqueous solution not lower than 30 mPa·s at 37° C.

The polyethylene oxide particles described herein further preferably have a viscosity of a 1% aqueous solution not lower than 30 mPa·s at 37° C.

In one embodiment, the biocompatible hemostatic product and the tissue sealant comprise PEO and at least one of biocompatible modified starch and polyvinylpyrrolidone (PVP), wherein the biocompatible modified starch has an average molecular weight ranging from 15,000 Daltons to 2,000,000 Daltons and is selected from at least one of pre-gelatinized starch, acid modified starch, esterified starch, etherified starch, graft starch, cross-linked starch and composite modified starch. In one preferable embodiment, the etherified starch comprises carboxymethyl starch and hydroxyethyl starch; the cross-linked starch comprises cross-linked carboxymethyl starch; the composite modified starch comprises pre-gelatinized hydroxypropyl distarch phosphate; the esterified starch comprises hydroxypropyl distarch phosphate; the graft starch comprises acrylic acid-carboxymethyl starch grafted copolymer and propylene ester-carboxymethyl starch grafted copolymer. More preferably, the biocompatible modified starch is carboxymethyl starch or a sodium salt thereof. In the biocompatible hemostatic product, the mass ratio between the polyethylene oxide particles and the biocompatible modified starch and/or polyvinylpyrrolidone can be adjusted by the skilled in the art as needed. For example, the mass ratio between the polyethylene oxide particles and the biocompatible modified starch can be varied from 9:1 to 1:9, preferably from 9:1 to 6:1; and the mass ratio between the polyethylene oxide particles and polyvinylpyrrolidone can be varied from 6:1 to 3:1. In the biocompatible hemostatic product comprising the polyethylene oxide particles and biocompatible modified starch as well as polyvinylpyrrolidone, the content of polyethylene oxide particles ranges from 99% to 5% by mass, the content of biocompatible modified starch ranges from 90% to 5% by mass; the content of polyvinylpyrrolidone ranges from 90% to 1% by mass.

In another embodiment, the biocompatible hemostatic product and the tissue sealant comprise one or more of pharmaceutically acceptable excipients, coagulants, anti-infectious medicament and anti-inflammation medicament, in addition to PEO particles. The pharmaceutically acceptable excipients include, but are not limited to, solvents, dispersion media, coating agents, surfactants, anti-oxidants, preservatives, isosmotic agents, delaying absorption agents, binding agents, lubricants, pigments and combination thereof or analogues thereof. The above pharmaceutically acceptable excipients are well known to those skilled in the art (see, e.g., "Remington's Pharmaceutical Sciences", $18^{th}$ edition, Mack Printing Company, 1990, pages 1289-1329, which is incorporated herein by reference in their entireties). The coagulants include, but are not limited to, one of gelatin, collagen, oxidized cellulose, carboxymethylcellulose, chitosan, hyaluronic acid, sodium alginate, kaolin, thrombin, fibrous protein, calcium, protamine, polypeptide, peptide and amino acid or combination thereof. The anti-infectious medicament includes, but is not limited to, one of antibiotics, anti-bacteria agents, anti-virus agents, anti-fungal agents, anti-ulcer agents, traditional Chinese medicine preparation and propolis or combination thereof. The anti-inflammation medicament includes, but is not limited to, one of non-steroid and steroid medicament, anti-ulcer medicament, traditional Chinese medicine preparation and propolis or combination thereof.

In another aspect, provided herein is a method for preparing a biocompatible hemostatic product and tissue sealant, including following steps:
(a) placing the polyethylene oxide particles with a viscosity-average molecular weight ranging from 100,000 Daltons to 7,000,000 Daltons, a particle size ranging from 0.5 µm to 2000 µm, a water absorbency capacity ranging from 1 to 500 times of its own weight, as raw material, into a granulator,
(b) adding solvents commonly used in granulating processes, such as purified water or distilled water, to the raw material that is placed into the granulator in step (a), and
(c) granulating at 40° C. to 50° C., and then sieving to obtain the biocompatible hemostatic product with a particle size ranging from 30 µm to 500 µm.

In one preferable embodiment, the method further includes adding at least one of a biocompatible modified starch and polyvinylpyrrolidone and/or at least one of pharmaceutically acceptable excipients, coagulants, anti-infectious medicament and anti-inflammation medicament to the raw material in step (a). Preferably, the biocompatible hemostatic product obtained in step (c) can be re-sieved to make the hemostatic product with a particle size ranging from 50 µm to 250 µm to account for higher than 70% in total hemostatic product.

In another preferable embodiment, the method further includes adding at least one of a biocompatible modified starch and polyvinylpyrrolidone and/or at least one of pharmaceutically acceptable excipients, coagulants, anti-infectious medicament and anti-inflammation medicament to the raw material after step (b) and before step (c). Preferably, the biocompatible hemostatic product obtained in step (c) can be re-sieved to make the hemostatic product with a particle size ranging from 50 μm to 250 μm to account for higher than 70% in total hemostatic product.

In an alternative embodiment, the biocompatible hemostatic product and tissue sealant provided herein can be prepared by a grafting method commonly used in the art, including following steps:
(a) modifying the surface of the polyethylene oxide particles by using a common grafting compound such as silicane, such that the surface of the polyethylene oxide particles adapts for covalent binding or ionic binding;
(b) swelling or dissolving the surface modified polyethylene oxide particles obtained in step (a) in water;
(c) adding at least one of a biocompatible modified starch and PVP to the solution of swollen or dissolved polyethylene oxide particles obtained in step (b), such that the at least one of a biocompatible modified starch and PVP is connected to the surface of the polyethylene oxide particles by covalent binding or ionic binding, thereby obtaining composite particles; and
(d) drying and sieving the composite particles obtained in step (c) to obtain the biocompatible hemostatic product with a particle size ranging from 30 μm to 500 μm.

In addition, the skilled in the art may utilize a common method in the art to prepare the biocompatible hemostatic product described herein into hemostatic aerosol, sponge, film, gel or patch. The skilled in the art may also use common method in the art to prepare the biocompatible tissue sealant into aerosol, film, sponge, gel or patch.

Moreover, the skilled in the art may utilize a common method in the art to apply the biocompatible hemostatic product described herein onto other hemostatic materials and fabrics to form hemostatic material with PEO coating, for example, modified starch hemostatic sponge with PEO coating, gelatin sponge with PEO coating, oxidized cellulose hemostatic gauze/film with PEO coating, chitosan hemostatic gauze/fiber with PEO coating, chitosan hemostatic sponge/film with PEO coating, sodium alginate hemostatic sponge with PEO coating and hemostatic bandage with PEO coating, hemostatic cotton with PEO coating, but not limited thereto.

The following methods are the ones used for preparing the above hemostatic products with PEO coating, but not limited to these methods:
Method 1: dissolving PEO particles in common solvents (e.g., water etc.), applying or spraying the PEO solution with a certain concentration onto the surface of other hemostatic material, and then drying to obtain hemostatic material with PEO coating.
Method 2: immersing other hemostatic material in aqueous solution (or other solvents) of PEO particles with a certain concentration, and then taking out and drying the hemostatic material to obtain hemostatic material with PEO coating.
Method 3: lyolysis (e.g., hydrolysis) of PEO particle, and then binding the PEO molecules onto the molecules of other hemostatic material via covalent binding or hydrogen binding, followed by using other methods commonly used in the art (including lyophilization, film-making, braiding) to obtain hemostatic material with PEO coating.

In yet another aspect, provided herein is the use of biocompatible hemostatic product and tissue sealant in hemostasis, avoiding adhesion, promoting tissue healing and/or wound sealing of either on the surface of tissue and organs or on tissues or organs within animal's body cavity. The animal includes, but is not limited to, primates, cows, sheep, goats, horses, dogs, cats, rabbits, rats, mice, fish, birds, and the like. Preferably, the animal is mammal. More preferably, the animal is a human.

In one embodiment, the biocompatible hemostatic product described herein is applied topically onto the bleeding wound surface during surgeries and trauma emergency treatment.

In another embodiment, the biocompatible hemostatic product described herein, for hemostasis and/or sealing tissue is applied onto a bleeding wound surface of the tissues and/or organs within the body's cavity by virtues of endoscope, to stop bleeding and seal the wound. The endoscope includes a nasoscope, laryngoscope, gastroscope, colonoscope, laparoscope, urology endoscope, hysteroscope and thoracoscope and so on. In one illustrative embodiment, the biocompatible hemostatic product of the present invention is applied topically onto a bleeding wound surface of the tissues or organs within body's cavity through EndoClot™ Hemostatic Powder and Spraying System (provided by a US Company—EndoClot Plus, Inc, see J Patel et al., PTU-029 The Use Of Endoclot™ Therapy In The Endoscopic Management Of Gastrointestinal Bleeding, *Gut,* 2014 63: A50-51 and K Halkerston et al., PWE-046 Early Clinical Experience of Endoclot™ in the Treatment of Acute Gastro-Intestinal Bleeding, *Gut,* 2013 62: A149) by virtues of endoscope. For example, the bleeding wound is caused by minimally invasive surgery or biopsy performed during Endoscopy. The skilled in the art would use the EndoClot™ Hemostatic Powder and Spraying System in combination with an endoscope according to the manufacturer's instructions for use, so as to apply the biocompatible hemostatic product described herein onto the bleeding wound surface in the body's cavity caused by minimally invasive Endoscopy, thereby stopping bleeding and sealing the wound.

The biocompatible hemostatic product described herein is able to absorb water from blood immediately after contacting the blood, so as to form a glue and glue-like clot. The glue and glue-like clot exhibit excellent viscosity and will adhere to the wound surface to seal the wound and stop bleeding. Moreover, the glue will not be degraded by the enzymes in the organism and thus adhere to the wound surface for a long time, thereafter, the glue will be peeled off with the scar.

Additionally, when the biocompatible hemostatic product and tissue sealant are topically sprayed within the digestive tract, the biocompatible hemostatic product and tissue sealant can interact with gastric fluid and exudate or saline administered by doctor, in addition to the blood from the wound, to form a hydrogel. The formed hydrogel and glue-like clot can also protect the wound surface, seal the wound, prevent the wound from stimulation by gastric fluid and intestinal fluid, avoid the infection of wound and promote wound healing. Since the biocompatible hemostatic product and tissue sealant described herein will not be easily degraded by digestive enzymes in the body, the formed glue will stay on the surface of the digestive tract for several hours or several days. Therefore, the biocompatible hemostatic product and tissue sealant described herein exhibit critical clinical significance for sealing and protecting of the ulcer surface and inflammation lesion on the inner wall of digestive tract, or the wound formed caused by minimally invasive surgery, surgery and trauma and the like, or the a wound surface rendered due to scald/burn/corrosion and the like caused by food, chemicals and medicaments. The said clinical significance includes, but is not limited to, hemostasis, topically sealing tissue, avoiding infection and promoting wound healing. Furthermore, addition of some medicaments to the above product will achieve the effect of topically controlled-release of the medicament and topical treatment in the digestive tract.

In addition, when the biocompatible hemostatic product and tissue sealant are topically sprayed onto the wound surface, the wound and lesion on the body surface and in the body, the biocompatible hemostatic product and tissue sealant can interact with body fluid including lymph fluid and oozing fluid and saline administrated by the doctor, in addition to the blood from the wound surface, to a form hydrogel. The formed hydrogel and glue-like clot can also protect the wound surface, seal the wound, prevent the wound from stimulation of topical bile and intestinal fluid, avoid the infection of wound and promote wound healing. Since the biocompatible hemostatic product and tissue sealant will not be degraded by digestive enzymes in the body, the formed glue will stay on the surface of wound or lesion for several hours to several days, so as to form a mechanical barrier for avoiding post-surgery tissue adhesion and promoting tissue healing. Furthermore, if some medicaments are added to the biocompatible hemostatic product, topically controlled-release of the medicament and topical treatment can be achieved, for the purpose of anti-infection and anti-tumor and the like.

In addition, when the biocompatible hemostatic product and tissue sealant are topically sprayed onto the wound surface, wound and lesion on the body surface and in the body, the biocompatible hemostatic product and tissue sealant can interact with body fluid including lymph fluid, intestinal fluid, chest fluid, exudation fluid from the wound and saline administrated by the doctor, in addition to the blood from the wound surface, to form a hydrogel. The formed hydrogel or glue-like clot can protect the wound surface, seal the wound, avoid intestinal fistula, biliary fistula, thoracic fistula, cerebrospinal fluid fistula, lymphatic fistula and reduce exudation and the like.

The biocompatible hemostatic product described herein can be packaged and sterilized using common methods in the art for ease of clinic use of the above biocompatible hemostatic product and tissue sealant. X-ray, ethylene oxide and ozone etc. can be used for sterilization. Preferably, ethylene oxide is used for sterilization.

DETAILED DESCRIPTION

Respective aspects of the present invention will be described in details as follows by referring to the following specific examples. Such examples merely intend to illustrate the present invention but not to limit the scope and the spirit of the present invention.

EXAMPLES

Example 1. Biocompatible Hemostatic Products Comprising PEO Particles

This example provides a series of biocompatible hemostatic products #1 to #4 comprising PEO particles with a wide range of viscosity-average molecular weight. The physicochemical parameters of PEO particles contained in these biocompatible hemostatic products and the particle sizes of the biocompatible hemostatic products are listed in Table 1.

TABLE 1

| No. | Chemical and physical characteristics of PEO particles |
|---|---|
| #1 | Viscosity-average molecular weight: 600,000D; particle size: 0.5 μm-2000 μm; water absorbency capacity: 5~15 times of its own weight |
| #2 | Viscosity-average molecular weight: 1,000,000D; particle size: 0.5 μm-2000 μm; water absorbency capacity: 5~15 times of its own weight |
| #3 | Viscosity-average molecular weight: 2,000,000D; particle size: 0.5 μm-2000 μm; water absorbency capacity: 5~15 times of its own weight |
| #4 | Viscosity-average molecular weight: 4,000,000D; particle size: 0.5 μm-2000 μm; water absorbency capacity: 5~15 times of its own weight |
| control | Arista ™ hemostatic powder (produced by American Medafor Inc.); Molecular weight: 5,000D-200,000D; particle size: 10 μm-350 μm, average particle size: 100 μm, water absorbency capacity: 5~10 times of its own weight Arista is a hemostatic powder proven by the FDA to use on the body surface or use within body, comprising microporous polysaccharide derived from plant starch, which is an effective hemostatic powder known in the art. |

The biocompatible hemostatic products #1 to #4 as mentioned above are prepared through following steps:
(a) placing the PEO particles with various viscosity-average molecular weight as raw materials into a granulator,
(b) adding distilled water into the raw materials that are placed into granulator in step (a), and
(c) granulating at 40° C. to 50° C., and then sieving to obtain biocompatible hemostatic products with a particle size ranging from 50 μm to 250 μm.

Figure 1A:
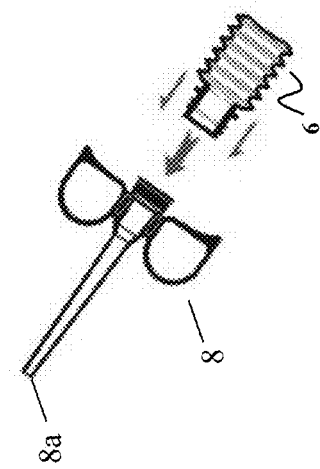
FIG. 1A shows a first step for applying the biocompatible hemostatic product and tissue sealant described herein through a spraying instrument according to the examples herein.
Figure 1B:
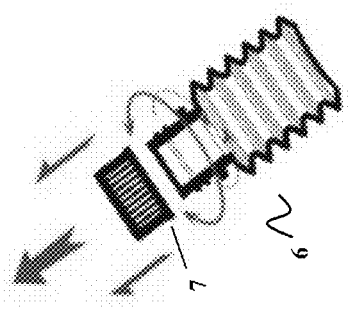
FIG. 1B shows a second step for applying the biocompatible hemostatic product and tissue sealant described herein through a spraying instrument according to the examples herein.
Figure 1C:
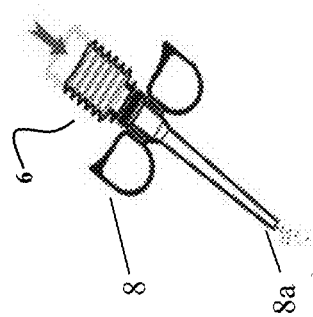
FIG. 1C shows a third step for applying the biocompatible hemostatic product and tissue sealant described herein through a spraying instrument according to the examples herein.
Figure 1D:
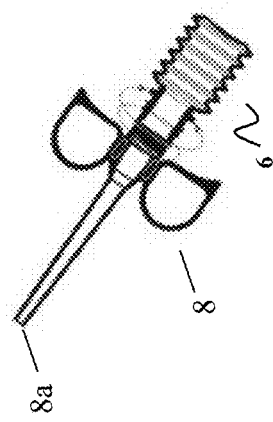
FIG. 1D shows a fourth step for applying the biocompatible hemostatic product and tissue sealant described herein through a spraying instrument according to the examples herein.

The biocompatible hemostatic products of this example and following examples can be sprayed onto a bleeding wound using a common method in the art, to detect the efficacy for hemostasis. Preferably, the biocompatible hemostatic products provided herein can be sprayed according to the steps as shown in FIGS. 1A to 1D. In particular, the biocompatible hemostatic products provided herein were firstly contained in a vessel 6 and the lid 7 of the vessel 6 was removed (as shown in FIG. 1A), next the vessel 6 in which the biocompatible hemostatic products were contained was connected with an applicator head 8 (as shown in FIG. 1B), then the applicator head was screwed on the vessel (as shown in FIG. 1C), the distal end 8a of the applicator head 8 was directed to the bleeding wound surface and the vessel 6 in which the biocompatible hemostatic products were contained was pressured, so that the biocompatible hemostatic products was sprayed to the bleeding wound (as shown in FIG. 1D).

The efficacy of the biocompatible hemostatic products #1 to #4 as mentioned above and control sample for hemostasis are detected using following method.

5 New Zealand white rabbits (provided by the animal experiment centre of The Second Military Medical University) were anesthetized by sodium pentobarbital via auricular vein and were fixed on overhead position, followed by deplumation and then the abdominal cavity was opened to completely expose the liver. A bleeding wound with a length of about 1 cm, width of about 1 cm and depth of about 0.3-0.4 cm was made on the surface of the liver of each rabbit by using a scalpel. After wiping the blood from the wound by gauze, samples #1 to #4 and control sample as listed in table 1 were immediately sprayed onto the wound, the dosage per spraying was about 1 g, and then the time and efficacy for hemostasis of samples #1 to #4 and control sample were observed.

In the above experiments on the liver, bleeding from the wound was stopped within 15 to 30 seconds after applying samples #3 and #4 and bleeding from the wound surface was stopped within 45 seconds to 1 minute after applying samples #1 and #2, while bleeding from the wound surface was stopped within 3 to 5 minutes after applying the control sample.

According to the observation and the experiments for efficacy of hemostasis, it can be seen that PEO particles with high viscosity-average molecular weight (e.g., samples #3 and #4) are able to rapidly concentrate blood to form a clot after contacting with blood, and the clot formed from PEO-blood has high viscosity and can be immediately adhered to the wound to seal the wound and effectively achieve hemostasis of vein. PEO particles with low viscosity-average molecular weight concentrate blood at a lower speed than PEO particles with high viscosity-average molecular weight after contact with blood and the clot formed thereafter has a lower viscosity than that of PEO particles with high viscosity-average molecular weight. Therefore, PEO particles with low viscosity-average molecular weight will take a longer time for hemostasis. However, the control sample concentrates blood at a much lower speed than PEO particles with high viscosity-average molecular weight and low viscosity-average molecular weight after contacting with blood, and the clot formed after contacting blood has a much lower viscosity, with poor efficacy for sealing. Therefore, the control sample takes a much longer time to achieve hemostasis.

In addition, the hemostatic products and the clot formed after the hemostatic products contacts blood will not be degraded by the amylase in the organism (while the hemostatic material of control sample can be rapidly degraded by amylase) and thus it is able to adhere on the wound surface for a long time. Therefore, the hemostatic products provided herein exhibit great efficacy on sealing wounds.

Example 2. Biocompatible Hemostatic Products Comprising PEO Particles and Carboxymethyl Starch (CMS)

This example provides a series of biocompatible hemostatic products #5 to #8 comprising PEO particles and carboxymethyl starch (CMS), or a sodium salt thereof, particles with a wide range of mass ratios there between, wherein PEO particles have a viscosity-average molecular weight of 2,000,000 D, a particle size ranging from 0.5 μm to 2000 μm and water absorbency capacity ranging from 5 to 15 times of its own weight, and CMS particles have a viscosity-average molecular weight ranging from 3,000 D to 200,000 D, a particle size ranging from 0.5 μm to 1000 μm, and water absorbency capacity ranging from 10 to 30 times of its own weight. The mass ratios between PEO particles and CMS particles contained in the biocompatible hemostatic products #5 to #8 of this example are listed in table 2. The control sample of this example is Arista hemostatic powder (produced by American Medafor Inc.) with a molecular weight ranging from 5,000 D to 200,000 D, a particle size ranging from 10 μm to 350 μm, and an average particle size of 100 μm, and water absorbency capacity ranging from 5 to 10 times of its own weight.

TABLE 2

| No. | mass ratio between PEO particles and CMS particles |
|---|---|
| #5 | 6:1 |
| #6 | 3:1 |
| #7 | 1:3 |
| #8 | 1:6 |

The biocompatible hemostatic products #5 to #8 as mentioned above are prepared through following steps:
(a) placing the PEO particles and CMS particles as raw materials in terms of a certain mass ratio into a granulator,
(b) adding distilled water into the raw materials that are placed into granulator in step (a), and
(c) granulating at 40° C. to 50° C., and then sieving to obtain biocompatible hemostatic products with a particle size ranging from 50 μm to 250 μm.

The efficacy of the biocompatible hemostatic products #5 to #8 as mentioned above and the control sample for hemostasis are detected using following method.

5 New Zealand white rabbits (provided by the animal experiment centre of The Second Military Medical University) were anesthetized by sodium pentobarbital via auricular vein and were fixed on overhead position followed by deplumation and then the abdominal cavity was opened to completely expose the liver. A bleeding wound with length of about 1 cm, width of about 1 cm and depth of about 0.3-0.4 cm was made on the surface of the liver of each rabbit by using a scalpel. After wiping the blood on the wound surface with gauze, samples #5 to #8 as listed in table 2 and the control sample were immediately sprayed onto the wound, the dosage per spraying is about 1 g, and then the efficacy of samples #5 to #8 and control sample for hemostasis was observed.

In the above experiments on the liver, bleeding from the wound was stopped within 15 seconds after applying samples #5 and #8 and bleeding from the wound was stopped within 3 to 5 minutes after applying the control sample. According to the experiments about efficacy for hemostasis, it can be seen that the hemostatic products comprising PEO particles and CMS particles rapidly concentrates blood after contacting with blood to form a clot and that the resulting clot has a high viscosity and thus can immediately attach to the bleeding wound to seal the wound and achieve hemostasis of the vein. However, the control sample concentrates blood at a lower speed than the experimental group after contact with the blood and the resulting clot has a lower viscosity than the experimental group, and thus it will take a long time for hemostasis.

Example 3. Biocompatible Hemostatic Products Comprising PEO Particles and Polyvinylpyrrolidone (PVP) Particles This example provides a series of biocompatible hemostatic products #9 to #11 comprising PEO particles and polyvinylpyrrolidone (PVP) particles with a wide range of mass ratios there between, wherein PEO particles have a viscosity-average molecular weight of 2,000,000 D, a particle size ranging from 0.5 μm to 2000 μm and a water absorbency capacity ranging from 5 to 15 times of its own weight, and PVP particles have a viscosity-average molecular weight of 90,000 D, a particle size ranging from 0.5 μm to 1000 μm, and a water absorbency capacity ranging from 5 to 15 times of its own weight. The mass ratios between PEO particles and PVP particles contained in the biocompatible hemostatic products #9 to #11 of this example are listed in table 3.

TABLE 3

| No. | Mass Ratio between PEO particles and PVP particles |
|---|---|
| #9 | 6:1 |
| #10 | 3:1 |
| #11 | 1:3 |

The biocompatible hemostatic products #9 to #11 as mentioned above are prepared through following steps:
(a) placing the PEO particles and PVP particles as raw materials in terms of a certain mass ratio into granulator,
(b) adding distilled water into the raw materials that are placed into granulator in step (a), and
(c) granulating at 40° C. to 50° C., and then sieving to obtain biocompatible hemostatic products with a particle size ranging from 50 μm to 250 μm.

The efficacies of the biocompatible hemostatic products #9 to #11 for hemostasis are detected using the method as described in Example 1. After applying samples #9 and #10 of this example, the bleeding from the wound was stopped within 30 seconds, while it took 3 to 5 minutes to completely achieve hemostasis for sample #11. By using samples #9 and #10, blood was concentrated rapidly and a clot was formed rapidly, while by using #11, blood was concentrated at a reduced speed and thus the clot was formed at a reduced speed as well. This may be because a large ratio of PVP has an influence on water absorbency. As a result, sample #11 took a long time to concentrate blood and thus had an influence on efficacy for hemostasis. Clots formed by samples #9 to #11 have high viscosity and can attach onto wounds for hemostasis of veins.

Example 4. Biocompatible Hemostatic Products Comprising PEO Particles, CMS Particles and PVP Particles This example provides a series of biocompatible hemostatic products #12 and #13 comprising PEO particles and PVP particles as well as CMS particles with a wide range of mass ratios, wherein PEO particles have a viscosity-average molecular weight of 2,000,000 D, a particle size ranging from 0.5 μm to 2000 μm and a water absorbency capacity ranging from 5 to 15 times of its own weight, CMS particles have a viscosity-average molecular weight ranging from 3,000 D to 200,000 D, a particle size ranging from 0.5 μm to 1000 μm and a water absorbency capacity ranging from 10 to 30 times of its own weight, and PVP particles have a viscosity-average molecular weight of 90,000 D, a particle size ranging from 0.5 μm to 1000 μm, and a water absorbency capacity ranging from 5 to 15 times of its own weight. The mass ratios among PEO particles, CMS particles and PVP particles contained in the biocompatible hemostatic products #12 and #13 of this example are listed in table 4.

TABLE 4

| No. | Mass Ratio among PEO particles, CMS particles and PVP particles |
|---|---|
| #12 | 1:3:1 |
| #13 | 6:3:1 |

The biocompatible hemostatic products #12 and #13 as mentioned above are prepared through following steps:
(a) placing PEO particles, CMS particles and PVP particles as raw materials in terms of a certain mass ratio into granulator,
(b) adding distilled water into the raw materials that are placed into granulator in step (a), and
(c) granulating at 40° C. to 50° C., and then sieving to obtain biocompatible hemostatic products with a particle size ranging from 50 μm to 250 μm.

The efficacy of the biocompatible hemostatic products #12 and #13 for hemostasis are detected by using the method as described in Example 1. After applying samples #12 and #13 of this example, the bleeding from the wound was stopped within 30 seconds. Blood was concentrated and a clot was formed immediately after samples #12 and #13 made contact with blood. Clots formed by samples #12 and #13 have a high viscosity and can rapidly attach onto a bleeding wound for hemostasis of veins.

The biocompatible hemostatic products of the above Examples 1 to 4 also can be prepared through the coating method, which includes the following steps:
(a) placing PEO particles as raw material into a granulator;
(b) adding water to the raw material of step (a) to cause the raw material to be swollen, (c) adding a certain mass ratio of CMS particles and/or PVP particles to the swollen PEO particles obtained in step (b), and (d) granulating at 40° C. to 50° C., and then sieving to obtain biocompatible hemostatic products with a particle size ranging from 50 μm to 250 μm.

The biocompatible hemostatic products of the above Examples 1 to 4 also can be prepared through the graft method commonly used in the art, including the following steps:

(a) modifying the surface of PEO particles using a common grafting compound such as silicane so that the surface of PEO particle adapts for covalent bonding or ionic bonding;

(b) dissolving or swelling the surface-modified PEO particles obtained in step (a) in water, (c) adding at least one of a biocompatible modified starch and a PVP to the solution of dissolved or swollen PEO particles obtained in step (b), so that the at least one of biocompatible modified starch and PVP is connected to the surface of PEO particles by covalent bonding or ionic bonding, thereby obtaining composite particles, and (d) washing, drying and sieving the composite particles, to obtain biocompatible hemostatic products with a particle size ranging from 30 μm to 500 μm.

Conclusion

Provided herein is a series of biocompatible hemostatic products, comprising PEO particles with a wide range of chemical and physical characteristics (e.g., water absorbency capacity and viscosity) and viscosity-average molecular weight as well as other polymers with certain chemical and physical characteristics (e.g., water absorbency capacity and viscosity and the like), such as biocompatible modified starch and PVP. From the efficacy for hemostasis of a series of biocompatible hemostatic products prepared in the above Examples 1 to 4, the biocompatible hemostatic products provided herein exhibit the efficacy of quick hemostasis after applying onto the bleeding wound. They exhibit efficacy for hemostasis and wound-sealing superior to commercial Arista™ hemostatic powder (produced by American Medafor Inc.) which is believed to have clinic effectiveness as is well known in the art.

Figure 2:
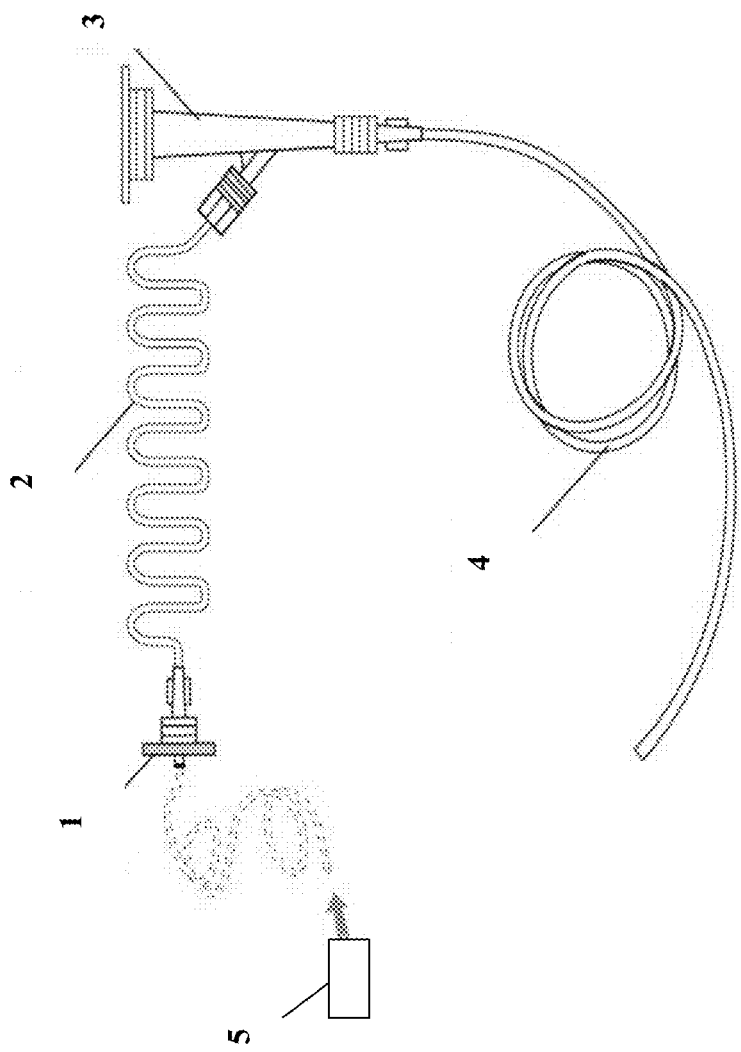
FIG. 2 is structural schematic diagram of EndoClot™ Hemostatic Powder and Spraying System.
Figure 3B:
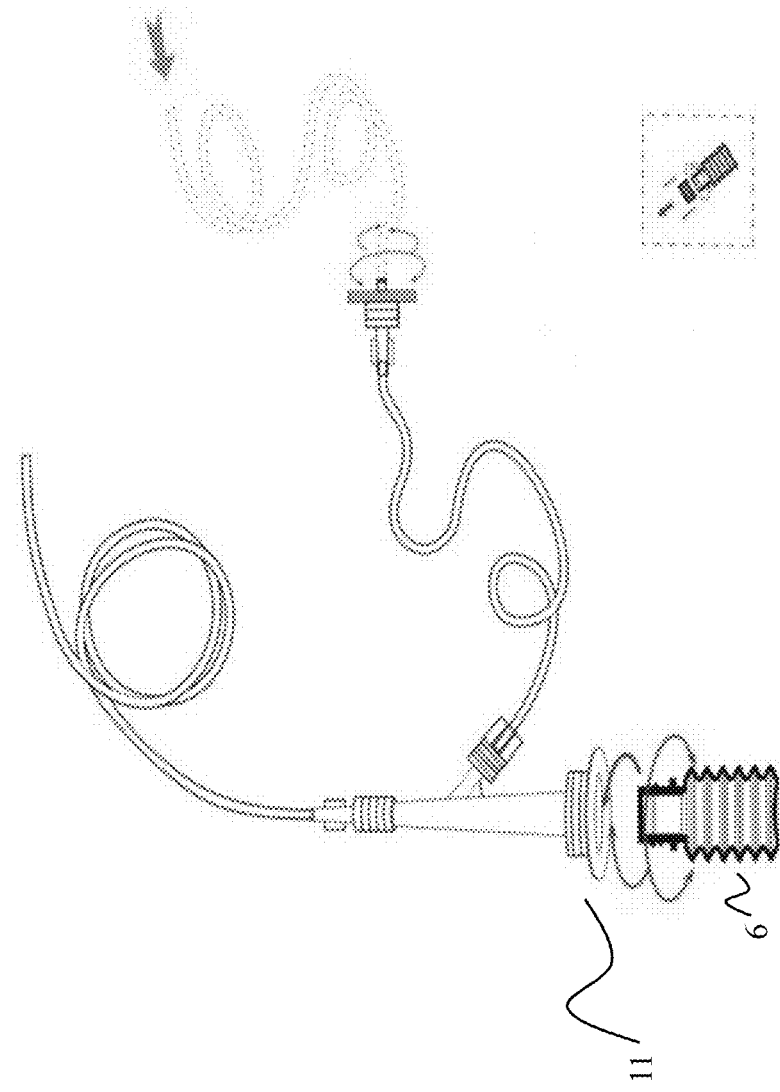
FIG. 3B shows a step for applying the biocompatible hemostatic product and tissue sealant described herein onto bleeding wound surface formed within body's cavity during minimally invasive surgery in the gastrointestinal tract using the system shown in FIG. 2, in an embodiment of the present specification.
Figure 3A:
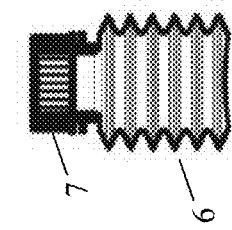
FIG. 3A shows a step for applying the biocompatible hemostatic product and tissue sealant described herein onto bleeding wound surface formed within body's cavity during minimally invasive surgery in the gastrointestinal tract using the system shown in FIG. 2, in an embodiment of the present specification.
Figure 3C:
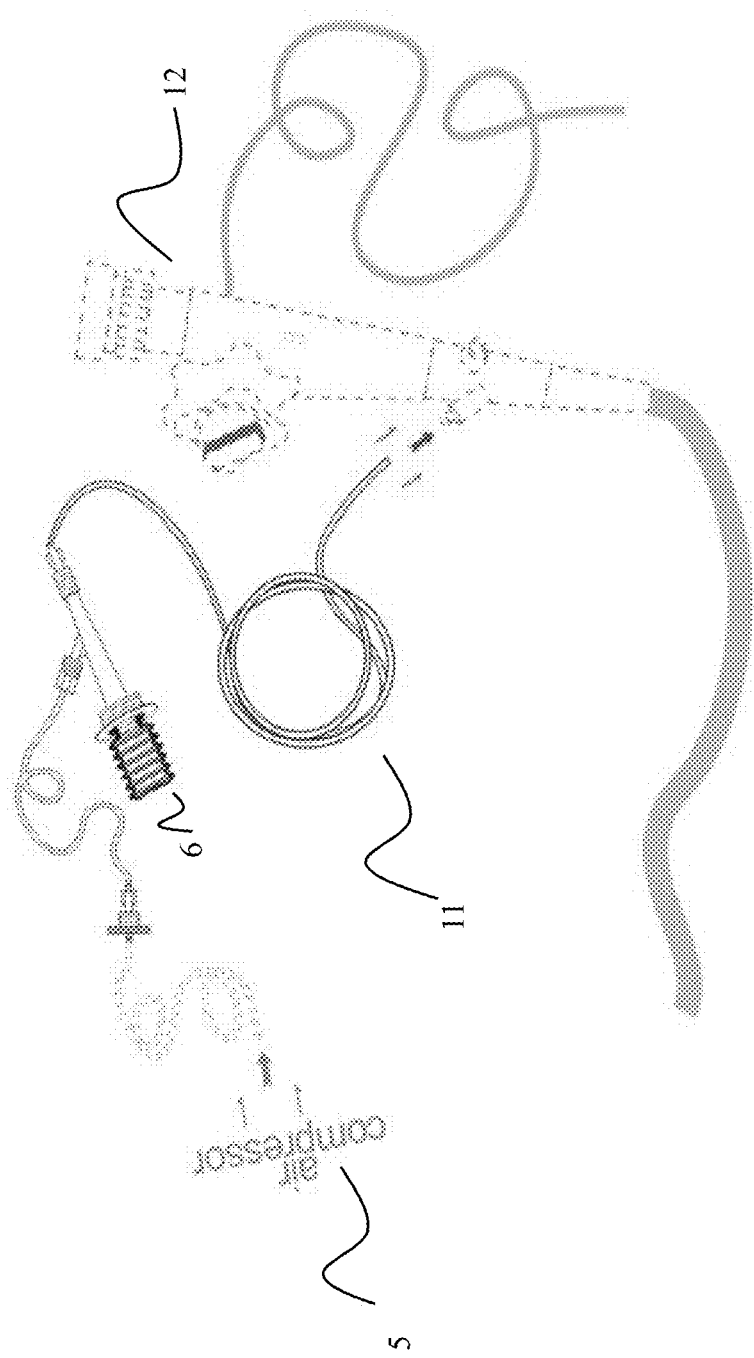
FIG. 3C shows a step for applying the biocompatible hemostatic product and tissue sealant described herein onto bleeding wound surface formed within body's cavity during minimally invasive surgery in the gastrointestinal tract using the system shown in FIG. 2, in an embodiment of the present specification; and, FIG. 3D shows a step for applying the biocompatible hemostatic product and tissue sealant described herein onto bleeding wound surface formed within body's cavity during minimally invasive surgery in the gastrointestinal tract using the system shown in FIG. 2, in an embodiment of the present specification.
Figure 3D:
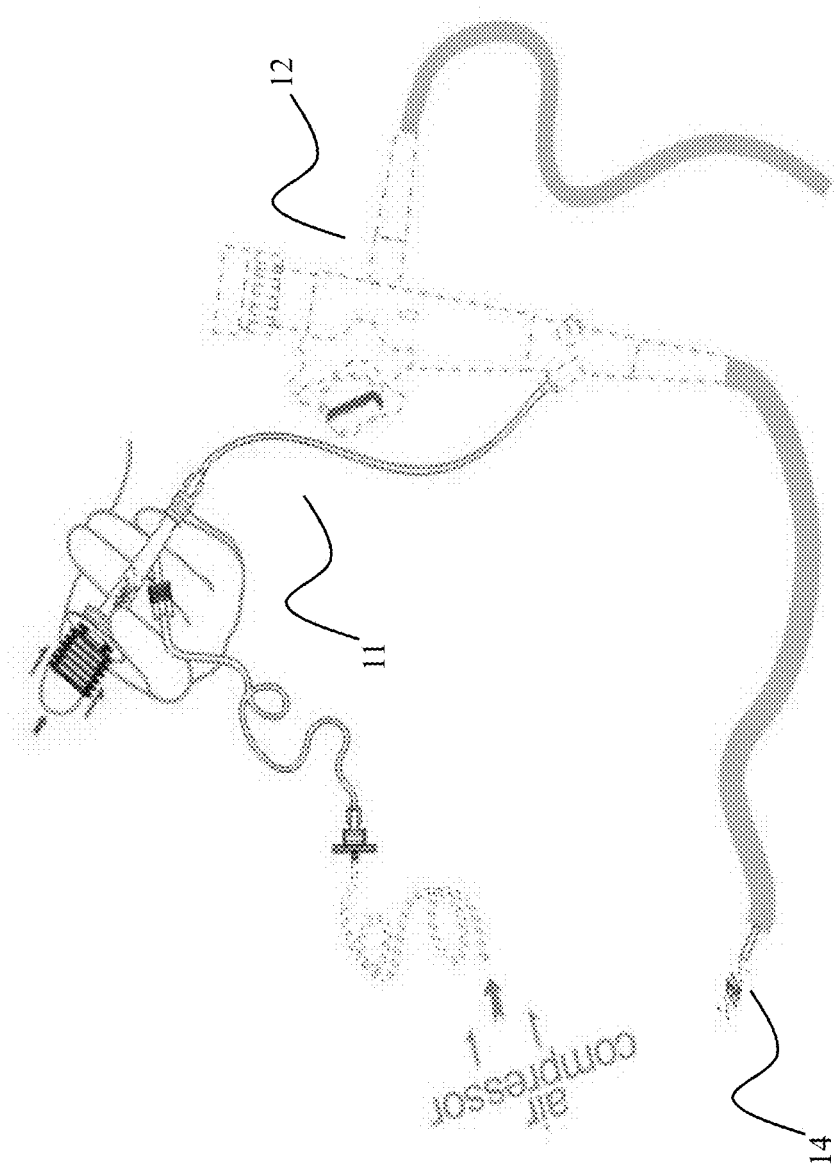

Example 5. Application of Biocompatible Hemostatic Products Provided Herein within Body's Cavity During minimally invasive surgery performed in the gastrointestinal tract, the biocompatible hemostatic products provided herein are applied onto a bleeding wound formed during minimally invasive surgery performed in the gastrointestinal tract by using EndoClot™ Hemostatic Powder and Spraying System (provided by US based company EndoClot Plus, Inc, usage method thereof sees J Patel et al., PTU-029 The Use Of Endoclot™ Therapy In The Endoscopic Management Of Gastrointestinal Bleeding, Gut, 2014 63: A50-51 and K Halkerston et al., PWE-046 Early Clinical Experience of Endoclot™ in the Treatment of Acute Gastro-Intestinal Bleeding, Gut, 2013 62: A149) via gastroscope and colonoscope for hemostasis and sealing wounds. The structural schematic diagram of the above EndoClot™ Hemostatic Powder and Spraying System is shown in FIG. 2. This Hemostatic Powder Spraying System includes a gas filter 1 that is connected to an air source 5 (or air pump), an air delivery catheter 2, a gas/powder mixing chamber 3 and attachments 4. The process for applying the the biocompatible hemostatic products of through this Hemostatic Powder and Spraying System via endoscope such as gastroscope and colonoscope includes following steps:

(a) adding the biocompatible hemostatic products provided herein to the sterilized vessel 6 (as shown in FIG. 3A) and removing the lid 7 of the vessel to connect to the EndoClot™ Hemostatic Powder and Spraying System 11 (as shown in FIG. 3B);

(b) switching on the air source 5 (or air pump) that is connected to the EndoClot™ Hemostatic Powder and Spraying System to keep the air flow pressure in the catheter into which biopsy forceps of gastro(colono) scope 12 is to be inserted in this system higher than the pressure in the patient's digestive tract (as shown in FIG. 3C);

(c) after performing biopsy on the lesion or removing the tissues (such as polyps or cancerous tissues) located on the inner wall of patient's digestive tract by the doctor using gastro(colono)scope 12, or after a wound occurs on the digestive tract (such as ulcer and inflammation wound surface), immediately inserting the catheter in this system into the biopsy passage of the gastro (colono)scope 12 and directing the distal end of the catheter 14 to the bleeding site (as shown in FIG. 3D);

(d) spraying the biocompatible hemostatic products to the bleeding wound in the digestive tract through the catheter (as shown in FIG. 3D) to rapidly concentrate blood and form a clot, such that the formed glue and glue-like clot will seal the wound to prevent further bleeding from the wound; and (e) withdrawing the catheter from the biopsy passage of the gastro(colono)scope after achieve hemostasis.

The present disclosure is described in details by referring to the specific examples. These examples are merely illustrative, but not intent to limit the scope of the present invention. One having the ordinary skill in the art would understand that many modifications, changes or substitutions may be made without departing from the spirit thereof. Thus, the equivalent variations according to the present invention come within the scope of the present invention.

What is claimed is:

1. A method of using a biocompatible hemostatic product to treat a wound within a body cavity of a patient, comprising applying an amount of the biocompatible hemostatic product to said wound,
wherein the biocompatible hemostatic product comprises polyethylene oxide particles,
wherein the polyethylene oxide particles have a viscosity-average molecular weight ranging from greater than 100,000 to 7,000,000 Daltons; and
wherein said amount is sufficient to cause at least one of hemostasis in said wound, sealing said wound, reducing exudation of said wound, promoting tissue healing around said wound, protecting a surface of said wound, or avoiding infection of said wound.

2. The method of claim 1 wherein the wound is located in at least one of the patient's respiratory tract, digestive tract, genital tract, or gastrointestinal tract.

3. The method of claim 1 wherein the polyethylene oxide particles have a particle size ranging from 0.5 μm to 2000 μm and a water absorbency capacity ranging from 1 to 500 times of their own weight.

4. The method of claim 1 wherein the biocompatible hemostatic product further comprises a biocompatible modified starch and wherein a ratio of a mass of said biocompatible modified starch to a mass of said polyethylene oxide particles ranges from 9:1 to 1:9.

5. The method of claim 4 wherein the biocompatible modified starch is selected from a group consisting of pre-gelatinized starch, acid modified starch, esterified starch, etherified starch, graft starch, cross-linked starch, composite modified starch, and combinations thereof.

6. The method of claim 5, wherein:
the etherified starch comprises carboxymethyl starch and hydroxyethyl starch;
the cross-linked starch comprises cross-linked carboxymethyl starch;
the composite modified starch comprises pre-gelatinized hydroxypropyl distarch phosphate;
the esterified starch comprises hydroxypropyl distarch phosphate; and
the graft starch comprises acrylic acid-carboxymethyl starch grafted copolymer and propylene ester-carboxymethyl starch grafted copolymer.

7. The method of claim 4, wherein the biocompatible modified starch is carboxymethyl starch or a sodium salt thereof.

8. The method of claim 1, wherein the biocompatible hemostatic product further comprises a biocompatible modified starch and polyvinylpyrrolidone, having a mass percentage of the biocompatible modified starch relative to a total mass of the biocompatible hemostatic product ranging from 5% to 90%, a mass percentage of polyvinylpyrrolidone relative to the total mass of the biocompatible hemostatic product ranging from 1% to 90%, and a mass percentage of the polyethylene oxide particles relative to the total mass of the biocompatible hemostatic product ranging from 99% to 10%.

9. The method of claim 1, wherein applying the biocompatible hemostatic product comprises:
passing a catheter through a channel of an endoscope, wherein the catheter is in fluid communication with an enclosed vessel and wherein said enclosed vessel contains the biocompatible hemostatic product; and
applying air flow pressure so as to direct said biocompatible hemostatic product from the vessel, through the catheter, and to said wound.

10. The method of claim 1, wherein the biocompatible hemostatic product further comprises at least one of pharmaceutically acceptable excipients, coagulants, anti-infectious medicament or anti-inflammation medicament, wherein:
the pharmaceutically acceptable excipients are selected from the group consisting of solvents, dispersion media, coating agents, surfactants, anti-oxidants, preservatives, isosmotic agents, delaying absorption agents, binding agents, lubricants, pigments and combinations thereof;
the coagulants are selected from the group consisting of gelatin, collagen, oxidized cellulose, carboxymethylcellulose, chitosan, hyaluronic acid, sodium alginate, kaolin, thrombin, fibrous proteins, calcium, protamine, polypeptides, peptides, amino acids and combinations thereof;
the anti-infectious medicament is selected from the group consisting of antibiotics, anti-bacterial agents, anti-virus agents, anti-fungal agents, anti-ulcer agents, traditional Chinese medicine preparation, propolis, and combinations thereof; and
the anti-inflammation medicament is selected from the group consisting of non-steroid and steroid medicaments, anti-ulcer medicaments, traditional Chinese medicine preparation, propolis and combinations thereof.

11. The method of claim 1, wherein a particle size of the polyethylene oxide particles ranges from 10 μm to 500 μm and a viscosity-average molecular weight of the polyethylene oxide particles ranges from 800,000 to 4,000,000 Daltons.

12. A method of using a biocompatible product to treat a wound within at least one of a patient's upper respiratory tract, digestive tract, genital tract, or gastrointestinal tract, comprising
using air pressure to apply an amount of the biocompatible product to said wound,
wherein the biocompatible product comprises polyethylene oxide particles,
wherein the polyethylene oxide particles have a viscosity-average molecular weight ranging from greater than 100,000 to 7,000,000 Daltons; and
wherein said amount is sufficient to cause at least one of hemostasis in said wound, sealing said wound, reducing exudation of said wound, promoting tissue healing around said wound, protecting a surface of said wound, or avoiding infection of said wound.

13. The method of claim 12 wherein said wound is at least one of an intestinal fistula, a biliary fistula, a thoracic fistula, or a lymphatic fistula.

14. The method of claim 12 wherein the polyethylene oxide particles have a particle size ranging from 0.5 μm to 2000 μm and a water absorbency capacity ranging from 1 to 500 times of their own weight.

15. The method of claim 12 wherein the biocompatible product further comprises a biocompatible modified starch and wherein a ratio of a mass of said biocompatible modified starch to a mass of said polyethylene oxide particles ranges from 9:1 to 1:9.

16. The method of claim 15 wherein the biocompatible modified starch is selected from a group consisting of pre-gelatinized starch, acid modified starch, esterified starch, etherified starch, graft starch, cross-linked starch, composite modified starch, and combinations thereof.

17. The method of claim 16, wherein:
the etherified starch comprises carboxymethyl starch and hydroxyethyl starch;
the cross-linked starch comprises cross-linked carboxymethyl starch;
the composite modified starch comprises pre-gelatinized hydroxypropyl distarch phosphate;
the esterified starch comprises hydroxypropyl distarch phosphate; and
the graft starch comprises acrylic acid-carboxymethyl starch grafted copolymer and propylene ester-carboxymethyl starch grafted copolymer.

18. The method of claim 15, wherein the biocompatible modified starch is carboxymethyl starch or a sodium salt thereof.

19. The method of claim 12, wherein the biocompatible hemostatic product further comprises a biocompatible modified starch and polyvinylpyrrolidone, wherein a mass percentage of the biocompatible modified starch relative to a total mass of the biocompatible hemostatic product ranges from 5% to 90%, a mass percentage of polyvinylpyrrolidone relative to the total mass of the biocompatible hemostatic product ranges from 1% to 90%, and a mass percentage of the polyethylene oxide particles relative to the total mass of the biocompatible hemostatic product ranges from 99% to 10%.

20. The method of claim 12, wherein applying the biocompatible product comprises:
using a catheter in fluid communication with an enclosed vessel, wherein said enclosed vessel contains the biocompatible hemostatic product;
passing the catheter through an endoscope; and
applying air flow pressure so as to direct said biocompatible hemostatic product from the vessel, through the catheter, and to said wound.

21. The method of claim 12, wherein the biocompatible product further comprises at least one of pharmaceutically acceptable excipients, coagulants, anti-infectious medicament or anti-inflammation medicament, wherein:
the pharmaceutically acceptable excipients are selected from the group consisting of solvents, dispersion media, coating agents, surfactants, anti-oxidants, preservatives, isosmotic agents, delaying absorption agents, binding agents, lubricants, pigments and a combination thereof;
the coagulants are selected from the group consisting of gelatin, collagen, oxidized cellulose, carboxymethylcellulose, chitosan, hyaluronic acid, sodium alginate, kaolin, thrombin, fibrous proteins, calcium, protamine, polypeptides, peptides, amino acids and a combination thereof;
the anti-infectious medicament is selected from the group consisting of antibiotics, anti-bacterial agents, anti-virus agents, anti-fungal agents, anti-ulcer agents, traditional Chinese medicine preparation, propolis, and a combination thereof; and
the anti-inflammation medicament is selected from the group consisting of non-steroid and steroid medicaments, anti-ulcer medicaments, traditional Chinese medicine preparation, propolis and a combination thereof.

22. The method of claim 12, wherein a particle size of the polyethylene oxide particles ranges from 10 μm to 500 μm and a viscosity-average molecular weight of the polyethylene oxide particles ranges from 800,000 to 4,000,000 Daltons.

23. A method of using a biocompatible product to treat a wound within at least one of a patient's upper respiratory tract, digestive tract, genital tract, or gastrointestinal tract, comprising:
passing a catheter through an endoscope, wherein
the catheter is in fluid communication with an enclosed vessel,
said enclosed vessel contains the biocompatible product,
the biocompatible product comprises at least one of polyethylene oxide particles, a combination of polyethylene oxide particles and biocompatible modified starch having a ratio of mass of the biocompatible modified starch to a mass of the polyethylene oxide particles ranging from 9:1 to 1:9, a combination of polyethylene oxide particles and polyvinylpyrrolidone, or a combination of polyethylene oxide particles, a biocompatible modified starch and polyvinylpyrrolidone having a mass percentage of the biocompatible modified starch relative to a total mass of the biocompatible hemostatic product ranging from 5% to 90%, a mass percentage of polyvinylpyrrolidone relative to the total mass of the biocompatible hemostatic product ranging from 1% to 90%, and a mass percentage of the polyethylene oxide particles relative to the total mass of the biocompatible hemostatic product ranging from 99% to 10%, and
the polyethylene oxide particles have a viscosity-average molecular weight ranging from greater than 100,000 to 7,000,000 Daltons; and
applying air flow pressure so as to direct an amount of said biocompatible product from the vessel, through the catheter, and to said wound, wherein said amount is sufficient to cause at least one of hemostasis in said wound, sealing said wound, reducing exudation of said wound, promoting tissue healing around said wound, protecting a surface of said wound, or avoiding infection of said wound.

24. The method of claim 23 wherein the polyethylene oxide particles have a particle size ranging from 0.5 μm to 2000 μm and a water absorbency capacity ranging from 1 to 500 times of their own weight.

* * * * *